(12) United States Patent
Utsunomiya (10) Patent No.: US 8,358,421 B2
(45) Date of Patent: Jan. 22, 2013

(54) OPTICAL TOMOGRAPHIC IMAGING APPARATUS THAT CHANGES REFERENCE BEAM PATH LENGTHS

(75) Inventor: Norihiko Utsunomiya, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 289 days.

(21) Appl. No.: 12/688,118

(22) Filed: Jan. 15, 2010

(65) Prior Publication Data

US 2010/0182610 A1 Jul. 22, 2010

(30) Foreign Application Priority Data

Jan. 22, 2009 (JP) .................................. 2009-011608

(51) Int. Cl.
*G01B 11/02* (2006.01)
(52) U.S. Cl. ........................................................ 356/497
(58) Field of Classification Search .................. 356/479, 356/497
See application file for complete search history.

(56) References Cited

U.S. PATENT DOCUMENTS

| | | | | |
|---|---|---|---|---|
| 6,198,540 | B1 * | 3/2001 | Ueda et al. ..................... | 356/479 |
| 7,557,931 | B2 | 7/2009 | Toida ............................. | 356/497 |
| 7,639,845 | B2 | 12/2009 | Utsunomiya | |
| 7,800,759 | B2 * | 9/2010 | Lai et al. ........................ | 356/497 |
| 7,872,760 | B2 * | 1/2011 | Ertl ................................ | 356/479 |
| 2007/0086011 | A1 | 4/2007 | Toida ............................. | 356/450 |
| 2009/0091766 | A1 | 4/2009 | Hirose .......................... | 356/479 |
| 2009/0285354 | A1 | 11/2009 | Hirose et al. ..................... | 378/19 |
| 2010/0002241 | A1 | 1/2010 | Hirose .......................... | 356/497 |
| 2010/0007894 | A1 | 1/2010 | Suehira ......................... | 356/497 |

FOREIGN PATENT DOCUMENTS

WO WO 2008/139799 A1 11/2008

OTHER PUBLICATIONS

Michael Pircher, et al. "Simultaneous SLO/OCT imaging of the human retina with axial eye motion correction," Optics Express, vol. 15, No. 25 (2007), pp. 16922-16932.
Tomasz Bajraszewski, et al. "Improved spectral optical coherence tomography using optical frequency comb," Optics Express, vol. 16, No. 6 (2008), pp. 4163-4176.

* cited by examiner

*Primary Examiner* — Hwa Lee
(74) *Attorney, Agent, or Firm* — Fitzpatrick, Cella, Harper & Scinto (57) ABSTRACT

In an optical tomographic imaging apparatus in which a tomographic image is acquired using an interference light between a return beam of a first measuring beam and a first reference beam traveling on a beam path having first beam path length changing unit thereon, an optical interferometer detects movement of the inspection object by using an interference light between a return beam of a second measuring beam from a movement detection position and a second reference beam traveling on a beam path having second beam path length changing unit thereon; and positional misplacement correcting unit changes the beam path length of the first reference beam based on the moving amount detected by the optical interferometer, wherein the beam path lengths of the two reference beams can be changed by a mechanism, thus further reducing deformation of an acquired image in an eye ball depth direction caused by a back and forth motion.

15 Claims, 8 Drawing Sheets

OPTICAL TOMOGRAPHIC IMAGING APPARATUS THAT CHANGES REFERENCE BEAM PATH LENGTHS

BACKGROUND OF THE INVENTION

1. Field of the Invention

The present invention relates to an optical tomographic imaging apparatus and, more particularly, to an optical tomographic imaging apparatus for use in opthalmological treatment or the like.

2. Description of the Related Art

Various kinds of optical equipment are currently used as ophthalmological equipment. Among them, there are various kinds of equipment used for observing an eye. For example, such equipment used includes an anterior ocular segment photographing device, a fundus camera, and a scanning laser ophthalmoscope (abbreviated as "an SLO"). Otherwise, also used is a low coherent optical tomographic imaging apparatus (optical tomographic imaging apparatus) and the like with an optical coherence tomography (abbreviated as "OCT") device (hereinafter referred to as "an OCT device"). Among them, the OCT device can obtain a tomographic image of a fundus in a high resolution, and therefore, it has become indispensable for out patient department specializing in a retinas.

The OCT device is adapted to irradiate a sample typified by a retina with a low coherent beam, so as to measure a beam reflected on the sample in a high sensitivity by using an interferometer. In addition, the OCT device can obtain a tomographic image by scanning the sample with the low coherent beam. In particular, a tomographic image of a retina is widely utilized for an ophthalmological diagnosis. Since the OCT device forms an image by scanning, there arises a problem that an involuntary motion of an eye ball called involuntary eye movement of a human eye ball or a back and forth motion of an eye ball including the whole head may deform an acquired image.

Conventionally, various attempts have been made to prevent the deformation of the image caused by the above-described motion of the human eye ball. For example, an OCT device for detecting the back and forth position of a cornea by using a low coherent interferometer is disclosed in the following literature: Christoph K. Hitzenberger, "Simultaneous SLO/OCT imaging of the human retina with axial eye motion correction," Optics Express, Vol. 15, No. 25 (2007). This device attempts to obtain the back and forth moving amount of an eye ball based on the resultant back and forth position detection value, and then, correct the reference beam path length of a low coherent optical tomographic imaging apparatus by the moving amount of the eye ball, so as to reduce deformation of the acquired image in the depth direction of the eye ball.

The above-described literature discloses the attempt of the reduction of the deformation in the depth direction of the eye ball. In contrast, the bandwidth of a light source has been widened in recent years, thereby further enhancing a resolution in the depth direction. Therefore, highly accurate correction beyond the prior art has been demanded.

The present invention has been accomplished in view of the above problem, and an object thereof is to provide an optical tomographic imaging apparatus capable of further reducing deformation of an acquired image in a depth direction of an eye ball caused by a back and forth motion of the eye ball during measurement.

SUMMARY OF THE INVENTION

The present invention provides an optical tomographic imaging apparatus such configured as described below.

There is provided an optical tomographic imaging apparatus, according to the present invention, in which a beam emitted from a light source is split into a first measuring beam and a first reference beam, the first measuring beam being guided to an inspection object whereas the first reference beam being allowed to travel on a beam path having first beam path length changing unit thereon, wherein a tomographic image of the inspection object is acquired by using an interference light between a return beam of the first measuring beam reflected on or scattered from the inspection object and the first reference beam traveling on the beam path having the first beam path length changing unit thereon, the optical tomographic imaging apparatus comprising: an optical interferometer which splits the beam emitted from one of the light source and another light source into a second measuring beam and a second reference beam so as to guide the second measuring beam to a position, at which movement of the inspection object is detected, and further, allow the second reference beam to travel on a beam path having second beam path length changing unit thereon, thus detecting moving amount of the inspection object by using an interference light between a return beam of the second measuring beam reflected on or scattered from the movement detection position of the inspection object and the second reference beam traveling on the beam path having the second beam path length changing unit thereon; and positional misplacement correcting unit provided on the beam path of the first reference beam independently of the first beam path length changing unit, for changing the beam path length of the first reference beam based on the moving amount of the inspection object detected by the optical interferometer, so as to reduce deformation of the tomographic image of the inspection object caused by a positional misplacement at the movement detection position of the inspection object, wherein the beam path length of the first reference beam by the positional misplacement correcting unit and the beam path length of the second reference beam by the second beam path length changing unit can be changed by a mechanism.

There is provided the optical tomographic imaging apparatus according to the above, wherein the light source for the optical interferometer is different from the light source for the optical tomographic imaging apparatus, the wavelength of the light source for the optical interferometer being different from that of the light source for the optical tomographic imaging apparatus.

There is provided the optical tomographic imaging apparatus according to the above, wherein the inspection object is an eye ball, and further, the optical interferometer is an optical interferometer for detecting a back and forth position caused by a back and forth motion of a cornea of the eye ball.

There is provided the optical tomographic imaging apparatus according to the above, wherein the beam path length of the first reference beam by the second beam path length changing unit can be controlled by a closed feedback system based on a detection result of the moving amount of the inspection object in the optical interferometer.

The present invention can implement the optical tomographic imaging apparatus capable of further reducing the deformation of the acquired image in the depth direction of the eye ball caused by the back and forth motion of the eye ball during the measurement.

Further features of the present invention will become apparent from the following description of exemplary embodiments with reference to the attached drawings.

DESCRIPTION OF THE EMBODIMENTS

Now, embodiments according to the present invention will be described below. First, description will be schematically made on the entire configuration of an optical tomographic imaging apparatus (i.e., a low coherent optical tomographic imaging apparatus) in the present embodiment with reference to FIG. 1. Here, the description will be made on a constitutional example in which an eye is inspected. In the optical tomographic imaging apparatus in the present embodiment, a beam emitted from a light source (a low coherent light source 101 for fundus tomography) for emitting a low coherent beam is split into a reference beam (a first reference beam) and a measuring beam (a first measuring beam). Then, the measuring beam is guided to a fundus of an eye to be inspected 119 as an inspection object; in contrast, the reference beam is guided to a reference optical path length adjusting device (a first optical path length adjusting device, or a reference beam path length adjusting stage 109). Thereafter, a return beam of the measuring beam reflected on or scattered from the fundus of the eye to be inspected is combined with the reference beam traveling through the reference optical path length adjusting device. Using the resultant interference signal (i.e., an interference light), the fundus of the eye to be inspected as the inspection object is acquired, so that a tomographic image is formed.

Here, it is desirable that a light source having a small time coherence and a large space coherence should be used as the low coherent light source 101 for fundus tomography. For example, a super luminescent diode, an ASE (Amplified Spontaneous Emission) light source, a femtosecond laser light source, and a wavelength-swept laser can be used. Both of a Michelson interferometer and a Mach-Zehnder interferometer may be used as an interferometer (a beam splitter 105) for splitting the beam emitted from the light source into the reference beam and the measuring beam, and then, combining them again, to allow them to interfere with each other. A beam path of the interferometer may be released in the air. Of course, the beam path may be constituted of an optical fiber system. The reference optical path length adjusting device can use a method for changing the beam length of the beam released in the air by a mirror placed on a stage or a method by use of a triangular prism placed on a rotary stage. A system for forming the tomographic image of the fundus of the eye to be inspected may be a combination of a time domain system, a spectral domain system, and a swept source system in which the wavelength-swept laser is used as the light source.

Next, a description will be given of the low coherent interferometer (an optical interferometer) for detecting a back and forth motion of an eye ball (i.e., the moving amount of an inspection object). The low coherent interferometer for detecting a back and forth motion of an eye ball according to the present invention splits the beam emitted from the light source for emitting the low coherent beam into a reference beam (a second reference beam) and a measuring beam (a second measuring beam), and then, guides the measuring beam to an eye ball movement detection position of the eye to be inspected (i.e., the movement detection position of the inspection object). In addition, a return beam of the measuring beam traveling on the reference beam path and reflected on or scattered from the movement detection position of the eye to be inspected is combined with a beam traveling on the reference beam path. And then, using the resultant interference signal, the back and forth position of the eye to be inspected after the back and forth movement is detected. The light source of the low coherent beam herein is identical to the above-described light source for fundus tomography. The beam emitted from the above-described light source for fundus tomography may be split on the beam path. Otherwise, another light source (i.e., a light source 121) may be used. Both of a Michelson interferometer and a Mach-Zehnder interferometer may be used as an interferometer for splitting the beam emitted from the light source into the reference beam and the measuring beam, and then, combining them again, to allow them to interfere with each other. A part of the beam path of the interferometer may be shared by the above-described interferometer for the fundus tomography. Alternatively, an independent beam path (a cornea position measuring beam path 124) may be used. Like the interferometer for the fundus tomography, the beam path may be released in the air or may be constituted of an optical fiber. Moreover, using the interference signal, the function of detecting the back and forth positional fluctuation of the eye to be inspected may be achieved by any of a time domain system, a spectral domain system, and a swept source system. From the viewpoint of a detection speed, the spectral domain system and the swept source system can be used.

Figure 1:
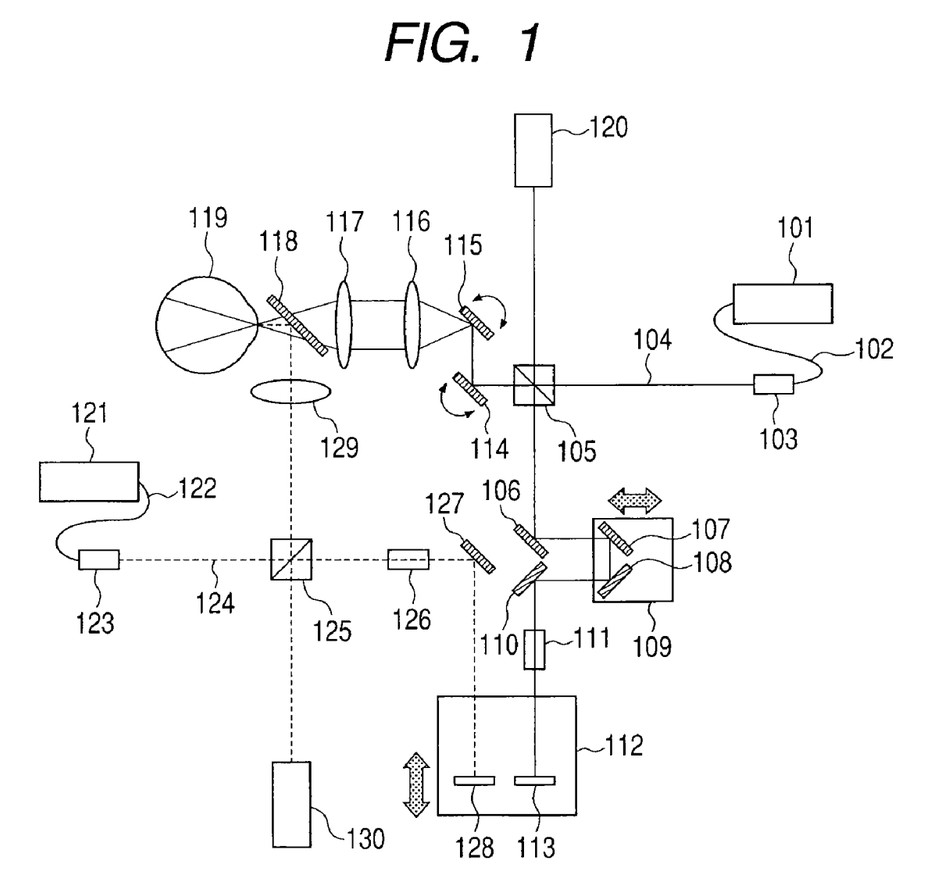
FIG. 1 is a diagram conceptually illustrating the entire configuration of an OCT device in a first embodiment according to the present invention.

Subsequently, a position misplacement correcting device will be explained below. The optical tomographic imaging apparatus in the present embodiment is provided with a position misplacement correcting device on the beam path of the reference beam in the optical tomographic imaging apparatus independently of the reference optical path length adjusting device (i.e., the first optical path length adjusting device). The position misplacement correcting device is adapted to vary the beam path length of the reference beam based on the moving amount of the inspection object, which is detected by the optical interferometer, so as to reduce deformation of the tomographic image of the inspection object due to a positional misplacement caused by the movement of the inspection object. In other words, a position misplacement correcting device (a tracking stage 112) is disposed on the reference beam path on the interferometer path in the low coherent optical tomographic imaging apparatus independently of the reference optical path length adjusting device (i.e., the reference beam path length adjusting stage 109). A straight stage can be used as the correcting device. Methods for driving the stage include a linear motor, a voice coil motor, and a piezo-electric actuator. However, the voice coil motor should be much preferable from the viewpoints of responsiveness and a drive stroke. In the present embodiment, one and the same mechanism can change the both of beam path length of the reference beam by the position misplacement correcting device and of the beam path length of the reference beam by a reference optical path length adjusting device (i.e., a second optical path length adjusting device) in the low coherent interferometer (i.e., the optical interferometer). As a consequence, the reference optical path length adjusting device for position misplacement correction can also correct at the same time a misplacement on the reference beam path in the low coherent interferometer for detecting the back and forth motion of the eye ball. Methods for correcting the misplacement at the same time include, for example, a tomographic mirror (a fundus tracking mirror 113) and a position detecting mirror (a cornea position tracking mirror 128) placed on the same stage, as illustrated in FIG. 1. Otherwise, one and the same mirror may correct the misplacement.

With the above-described configuration, the back and forth position of the eye ball detected by the low coherent interferometer for the position misplacement correction becomes constant all the time as long as the correction is made accurately. When there is a residual difference of the correction, the back and forth position is deviated. However, a drive command is given to the above-described optical path length adjusting device based on the misplacement from a predetermined position, and therefore, the residual difference is slight, if any. As a consequence, even if the eye ball is largely moved in the back and forth direction, the misplacement is sequentially corrected, so that the position of the eye ball cannot be deviated from the predetermined position in the low coherent interferometer for the detection. Namely, even the large back and forth motion of the eye ball can be corrected.

With the above-described configuration, the correction amount at the time of the measurement is reflected on the measurement result by the low coherent interferometer for measuring the back and forth position of the eye ball, thereby performing the control based on a latest correction residual difference all the time so as to achieve the highly accurate correction. The beam path length of the first reference beam by the second optical path length adjusting device can be controlled by a closed feedback system which refers to the detection result of the moving amount of the inspection object in the optical interferometer. That is to say, the closed feedback system is configured in such a manner as to use the positional fluctuation by the low coherent interferometer for measuring the back and forth position of the eye ball as it is as position control information for the device for correcting the back and forth positional fluctuation of the eye ball. In this manner, a control response can be sped up. Consequently, followability to the motion of the eye ball which is sequentially fluctuated can be enhanced, thus increasing control accuracy.

EMBODIMENTS

Embodiments according to the present invention will be described below.

First Embodiment

In a first embodiment, a description will be given of the configuration of an OCT device, to which the present invention is applied. FIG. 1 is a diagram conceptually illustrating the entire configuration of the OCT device in the present embodiment. In FIG. 1, there are illustrated a low coherent light source 101 for fundus tomography, an optical fiber 102, a fiber collimator 103, a fundus photographing beam path 104, a beam splitter 105, a mirror 106, a first reference mirror 107, a second reference mirror 108, a reference beam path length adjusting stage 109, a mirror 110, a dispersion compensating glass 111, a tracking stage 112, a fundus tracking mirror 113, a galvano scanner X 114, a galvano scanner Y 115, a first lens 116, a second lens 117, a dichroic mirror 118, and an eye to be inspected 119. Examples of an OCT include a Michelson interferometer. Examples of an interferometer for detecting a back and forth motion of an eye ball also include a Michelson interferometer. A top of a cornea of an anterior ocular segment of the eye ball is designed to be detected when the back and forth motion of the eye ball is detected.

Next, the configuration of an optical tomographic imaging apparatus system will be explained below. In the present embodiment, the low coherent light source 101 for fundus tomography has a center wavelength of 840 nm, and uses an SLD light source having a half-value width of 50 nm. The beam is guided to the fiber collimator 103 via the single mode fiber 102. The beam collimated by the fiber collimator travels on the beam path 104, and then, is split to a reference beam and a signal light by the beam splitter 105. The beam on the path 104 indicated by a solid line in FIG. 1 is a beam for use in fundus tomography. Out of the beams split by the beam splitter 105, the beam traveling on a reference beam path is guided, by the mirror 106, to the reference beam path adjusting device including the straight stage 109 and the beam path length adjusting mirrors 107 and 108. Here, a fundus image is adjusted in such a manner as to be contained within a screen by operation of the straight stage 109. The straight stage is a ball screw stage which is driven by a stepping motor. Furthermore, the reference beam is guided to the position misplacement correcting device including the tracking stage 112 and the mirrors 113 and 128 through the dispersion compensating glass 111 via the mirror 110. The tracking stage is driven based on a positional misplacement of an eye ball detected by an eye ball position detecting device, described later. A linear stage using a voice coil motor is used as the tracking stage. The reference beam turned over by the mirror 113 on the tracking stage passes the beam splitter 105 on the same beam path, and then, is combined with a signal light, described later, to travel toward a detector 120. The detector is an OCT of a spectral domain system in this configuration, thereby constituting a spectroscope. Here, although the spectroscope is not illustrated since it is irrelevant to the essence of the invention, it is of a polychroic meter type using a transparent grating and a line sensor.

In contrast, the signal light obtained by splitting the beam by the beam splitter 105 is guided to the galvano scanners 114 and 115 for scanning a fundus. The galvano scanner 114 is adapted to scan the fundus in an X direction (i.e., in a horizontal direction) whereas the galvano scanner 115 is adapted to scan the fundus in a Y direction (i.e., in a vertical direction). The beams deflected by the scanners are guided to the eye to be inspected 119 through the lenses 116 and 117. The beams deflected by the scanners are designed such that their incident angles are deflected again on and around an iris, thereby scanning the fundus of the eye to be inspected. The signal light scattered from or reflected on the fundus travels on the same beam path, and then, is combined with the reference beam by the beam splitter 105, to be thus guided to the detector 120. The detector 120 detects a signal indicating an interference between the reference beam and the signal light. The spectroscope receives the interference signal as a signal per wavelength. FFT signal processing is performed in response to the signal per wavelength, thereby obtaining information in a depth direction, so as to display a tomographic image.

Next, the configuration of an anterior ocular segment position detecting optical system will be described below. A beam emitted from a light source 121 is guided to a fiber collimator 123 through a single mode optical fiber 122. The wavelength of the beam can be readily distinguished from the wavelength of the beam for the fundus tomography, and further, the beam need not reach the fundus. Therefore, the light source used herein has a center wavelength of 1290 nm and uses an SLD light source having a half-value width of 50 nm. A broken line 124 indicates a beam for detecting an anterior ocular segment position. A beam splitter 125 splits the beam into a reference beam and a signal light. The reference beam is guided to the mirror 128 on the tracking stage 112 through a dispersion compensating glass 126 and a mirror 127. The beam turned over by the mirror travels on the same beam path, and then, is combined with the signal light by the beam splitter 125, to be thus guided to a detector 130. In contrast, the signal light is reflected on the dichroic mirror 118 through a lens 129 from the beam splitter 125, to thus reach the cornea of the eye to be inspected 119. The dichroic mirror 118 is adapted to reflect the beam having a wavelength of about 1290 nm whereas to transmit the beam having a wavelength of about 840 nm. The lens 129 is adjusted to have a focal distance and be located at a position where the beam focuses at the position of the cornea of the eye to be inspected. The beam reflected on the cornea travels on the same beam path, returns to the beam splitter 125, to be combined with the reference beam, and then, reaches the detector 130. The detector 130 is of a spectral domain type, and therefore, it is a polychroic meter spectroscope including a camera using a line sensor including a transparent grating and InGaAs. The signal detected by the spectroscope is subjected to FFT signal processing, thereby detecting the position of the cornea.

Figure 4A:
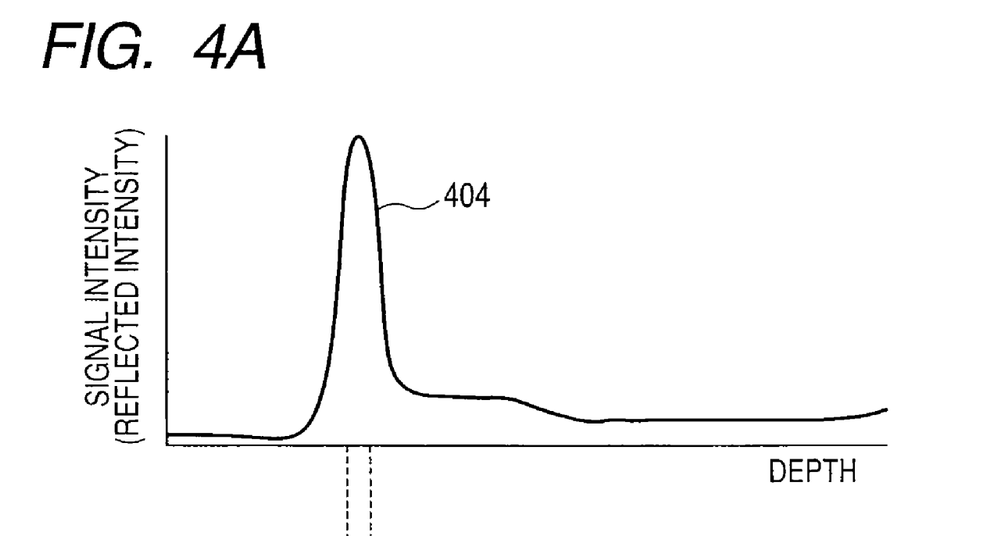
FIGS. 4A and 4B illustrate an image of an output signal and a cross-sectional image of a cornea, respectively, for use in positional detection in the first embodiment according to the present invention.
Figure 4B:
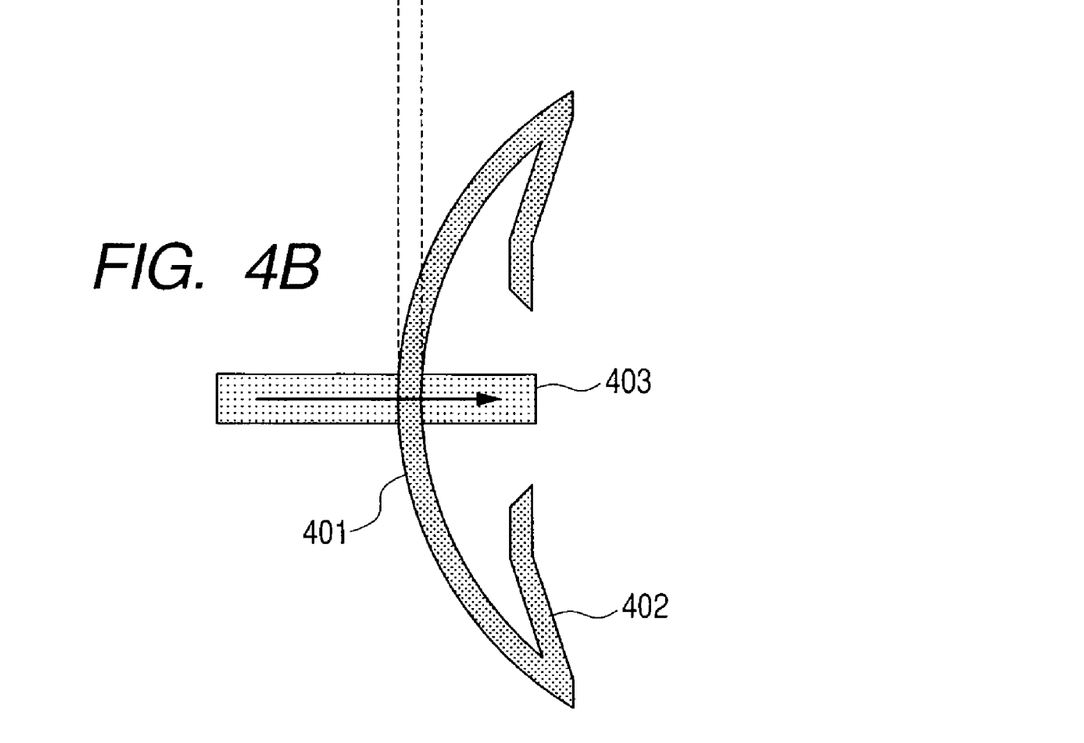

Next, a correcting method based on the anterior ocular segment position detection will be described below. FIGS. 4A and 4B illustrate an image of an output signal and a cross-sectional image of a cornea, respectively, for use in the positional detection in the present embodiment. FIG. 4A illustrates the image of an output signal; FIG. 4B illustrates the cross-sectional image of the cornea. There are illustrated a cornea 401, an iris 402, and a detection beam 403. A signal of a reflection component at the cornea has a peak 404. The positional misplacement of the peak 404 is detected, and then, drive force of the stage is controlled based on the positional misplacement.

Specifically, when the eye ball is displaced in the back and forth direction, the peak 404 is moved laterally in FIG. 4A. At this time, when the eye ball is displaced to the anterior direction, the peak is shifted leftward; in contrast, when the eye ball is displaced to the posterior direction, the peak is shifted rightward. A target peak has been defined in advance. Based on a misplacement from the target peak (so-called deviation), each of the deviation, an integral value of the deviation, and differential value of the deviation is multiplied by a gain, so that the drive force of the stage is determined.

Figure 7:
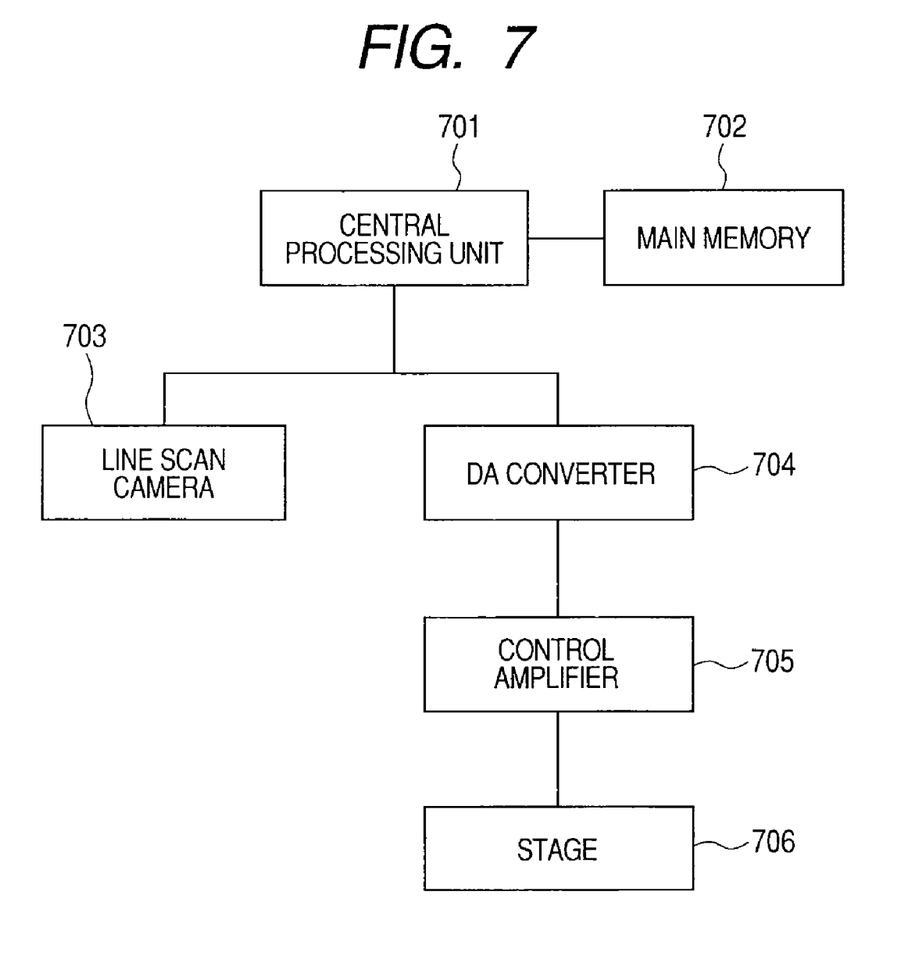
FIG. 7 is a block diagram illustrating a control unit for implementing a stage control in the first embodiment according to the present invention.

Subsequently, a flow of the control will be described with reference to FIGS. 7 and 8. FIG. 7 is a block diagram illustrating a control unit for implementing a stage control in the present embodiment. Here, the function of displaying the tomographic image of the fundus is omitted for the sake of simple explanation. A central processing unit 701 performs calculation relative to the control. A main memory 702 serves as a primary memory for data obtained by calculation. A line scan camera 703 is configured inside of the detector for detecting the back and forth position of the eye ball. A DA converter 704 is configured to provide an output during the control. A control amplifier 705 is configured to control the voice coil motor. A stage 706 is provided with the voice coil motor for correcting the back and forth misplacement.

Figure 8:
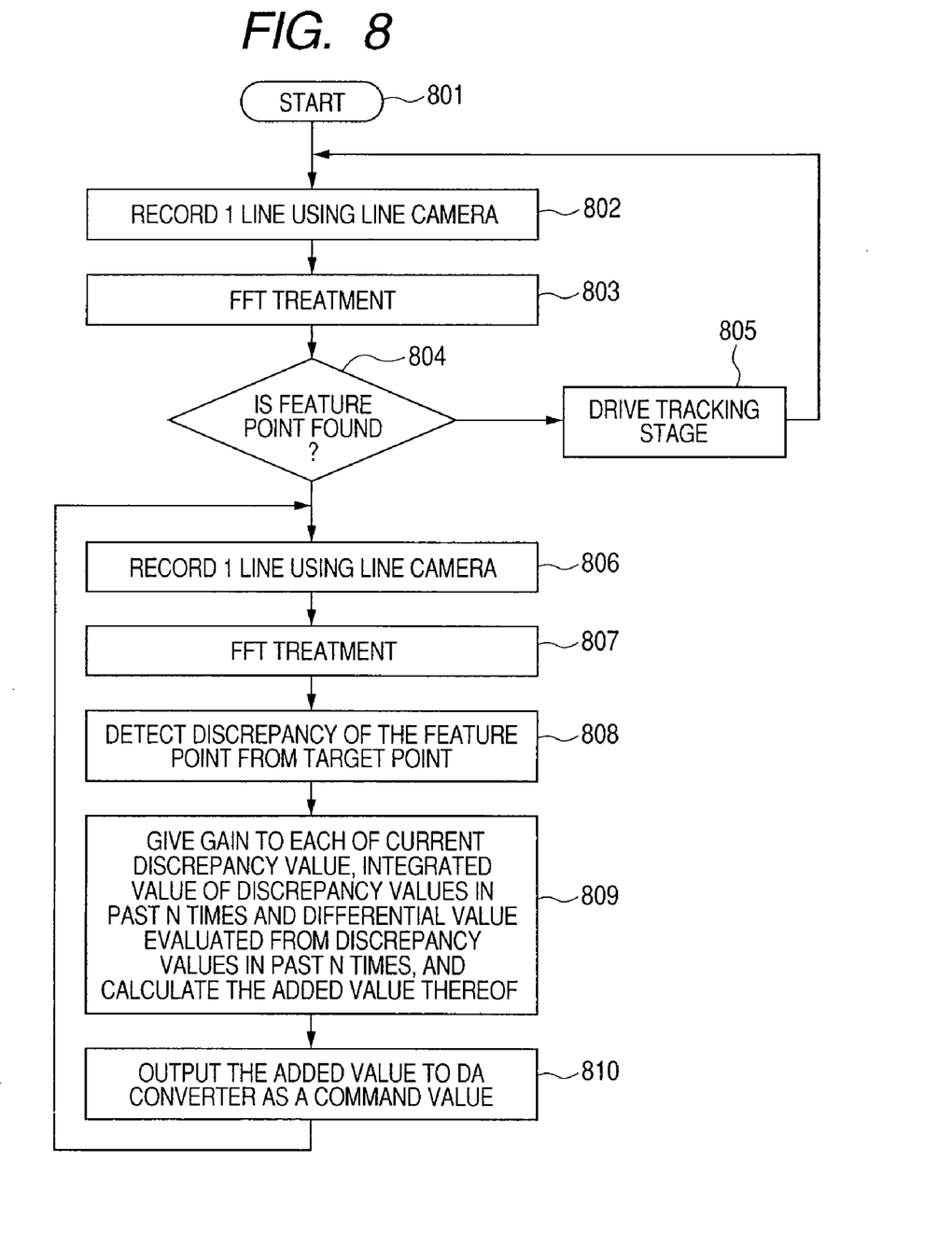
FIG. 8 is a flowchart illustrating the stage control in the first embodiment according to the present invention.

FIG. 8 is a flowchart illustrating the stage control in the present embodiment. When the processing is started in step 801, data of one line is first acquired from the line camera in step 802. The data indicates a spectrum, and therefore, the data is converted into a wavenumber. Then, the FFT treatment is performed in step 803. The FFT treatment leads to an output of a signal corresponding to a depth. It is determined in step 804 whether a feature point indicating the cornea is included in the signal. If it is found that there is no feature point in step 804, the voice coil stage is driven by amount defined in advance in step 805, and then, the procedure returns to step 802. The cornea is automatically searched till its detection by repeating the loop. Upon the detection of the cornea, data of one line is acquired from the line scan camera in step 806, and then, the FFT treatment is performed in step 807, like step 803. As a result, a misplacement from the target value set in advance in step 808 is determined. In step 809, an integral value and a differential value are determined based on a current misplacement and data in past N times (N is a proper value varied according to control systems, which is determined by acquiring data in advance). A control value obtained by summing gains set for each of the values is calculated. The control value is output into the DA converter in step 810. The output value in the DA converter is converted into an output current in substantial proportion to the position of the stage by the amplifier 705 illustrated in FIG. 7. Consequently, the drive is performed by adequate amount. The repetition of this operation enables the control in such a manner that the back and forth motion of the eye ball is not reflected on the movement of the tomographic image.

Second Embodiment

Figure 2:
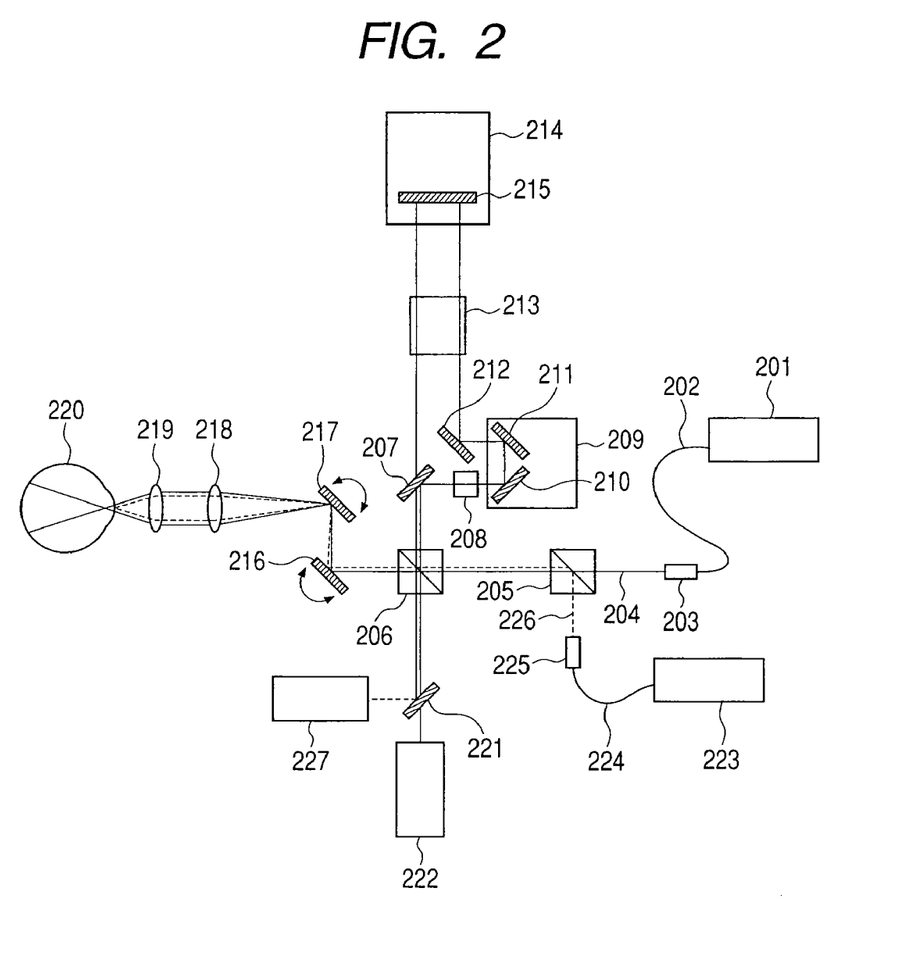
FIG. 2 is a diagram conceptually illustrating the entire configuration of an OCT device in a second embodiment according to the present invention.

A second embodiment exemplifies an OCT device having a configuration in which a beam path of a low coherent beam interferometer for detecting a back and forth motion of an eye ball is shared by an OCT device for fundus tomography. FIG. 2 is a diagram conceptually illustrating the entire configuration of an OCT device in the present embodiment. In FIG. 2, there are illustrated a low coherent light source 201 for fundus tomography, an optical fiber 202, a fiber collimator 203, a fundus photographing beam path 204, a beam splitter 205, another beam splitter 206, a dichroic mirror 207, a dispersion compensating glass 208, a reference beam path length adjusting stage 209 for a fundus, a reference beam path length adjusting mirror 210, another reference beam path length adjusting mirror 211, a mirror 212, a dispersion compensating glass 213, a tracking stage 214, a tracking mirror 215, a galvano mirror X 216, a galvano mirror Y 217, a first lens 218, a second lens 219, an eye to be inspected 220, a dichroic mirror 221, a fundus detector 222, a cornea low coherent light source 223, an optical fiber 224, a fiber collimator 225, a cornea detecting beam path 226, and a cornea position detector 227. In the present embodiment, a light source for tomography and a light source for motion detection use different wavelengths. The motion of a cornea is to be detected. Both of interferometers share most of the beam paths in a Michelson interferometer.

Next, the configuration of an optical tomographic imaging apparatus system will be explained below. In the present embodiment, the light source for tomography has a center wavelength of 840 nm, and uses an SLD light source having a half-value width of 50 nm. The beam is guided to the fiber collimator 203 by the single mode fiber 202. The beam collimated by the fiber collimator travels on the beam path 204 indicated by a solid line. The beam is combined with a beam for detecting the motion of an eye ball by the beam splitter 205. The resultant beam is split into a reference beam and a signal light by the beam splitter 206. The reference beam travels through the dichroic mirror 207.

The beam for the fundus tomography herein is reflected to travel through the dispersion compensating glass 208, and then, passes via the mirror 212 through a reference optical path length adjusting device including the mirrors 210 and 211 placed on the stage 209. Moreover, the beam reaches a tracking reference optical path length adjusting device including the tracking stage 214 and the mirror 215 through the other dispersion compensating glass 213. The beam turned over by the mirror 215 travels on the same beam path again, and then, returns to the beam splitter 206. Thereafter, the beam is combined with the signal light. Only a tomographic beam passes through the dichroic mirror 221, and thus, reaches the detector 222.

In contrast, the signal light obtained by splitting the beam by the beam splitter 206 reaches the eye to be inspected 220 through the lenses 218 and 219 via the galvano scanners 216 and 217. The signal light scattered from or reflected on the fundus of the eye to be inspected travels on the same beam path, passes through the beam splitter 206, is combined with the reference beam, passes through the dichroic mirror 221, and reaches the detector 222. The detector detects an interference signal between the signal light and the reference beam. A flow for forming an image from the interference signal is identical to that in the first embodiment, and therefore, description thereof will not be repeated.

Next, the configuration of an anterior ocular segment position detecting optical system will be described below. The beam emitted from the light source 223 is guided to the fiber collimator 225 through the single mode optical fiber 224. The wavelength of the beam can be readily distinguished from the wavelength for the fundus tomography and the beam need not reach the fundus, and therefore, the light source has a center wavelength of 1290 nm and uses an SLD light source having a half-value width of 50 nm. A broken line 226 indicates a beam for detecting an anterior ocular segment position. The beam splitter 205 combines the beam with the beam for the fundus tomography. The beam splitter 206 splits the beam into a reference beam and a signal light. The reference beam reaches the tracking reference optical path length adjusting device including the stage 214 and the mirror 215 through the dichroic mirror 207 and the dispersion compensating glass 213. The reference beam turned over by the mirror 215 travels on the same beam path, and then, returns to the beam splitter 206. The beam is combined with the signal light by the beam splitter, is reflected on the dichroic mirror 221, and then, reaches to the detector 227.

In contrast, the signal light obtained by splitting the beam by the beam splitter 206 reaches the cornea of the eye to be inspected 220 via the lenses 218 and 219 through the galvano scanners 216 and 217. The signal light reflected on or scattered from the cornea travels on the same path, and then, reaches the beam splitter 206. The beam is combined with the reference beam, is reflected on the dichroic mirror 221, and thus, reaches the detector 227. The detector 227 is the same spectrometer as that in the first embodiment.

Figure 5A:
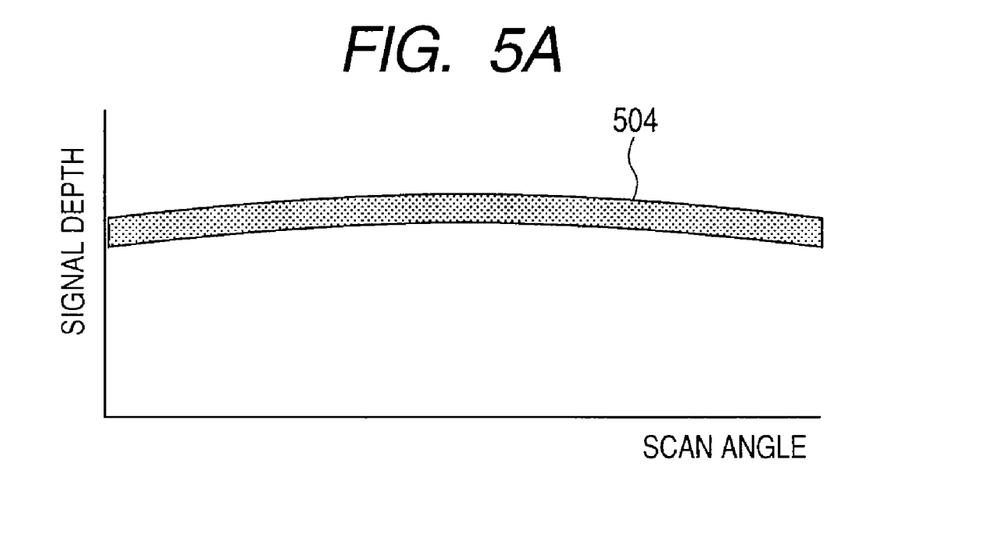
FIGS. 5A and 5B illustrate images of detection of a position of an eye ball in the second embodiment according to the present invention.
Figure 5B:
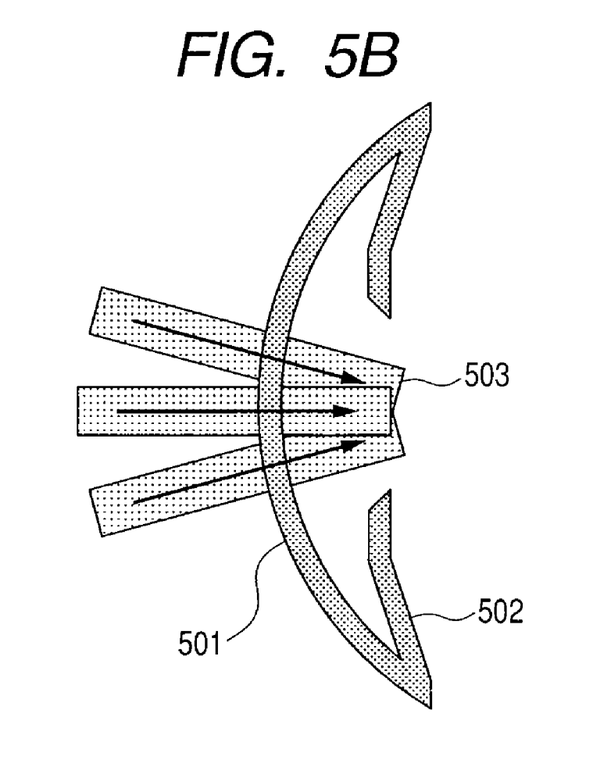

Next, a correcting method based on the anterior ocular segment position detection will be described below. FIGS. 5A and 5B illustrate an image of an output signal and a cross-sectional image of a cornea, respectively, for use in positional detection in the present embodiment. FIG. 5A illustrates the image of an output signal. In the present embodiment, since scanning is carried out with a position detecting beam, an image illustrated in FIG. 5A is acquired. FIG. 5B illustrates the cross-sectional image of the cornea. There are illustrated a cornea 501, an iris 502, and a detection beam 503. A signal of a reflection component at the cornea is expressed by a curve 504. The maximum position of the signal 504 is obtained, and then, drive force of the stage is controlled based on the positional misplacement. A control method is the same as that in the first embodiment.

Third Embodiment

Figure 3:
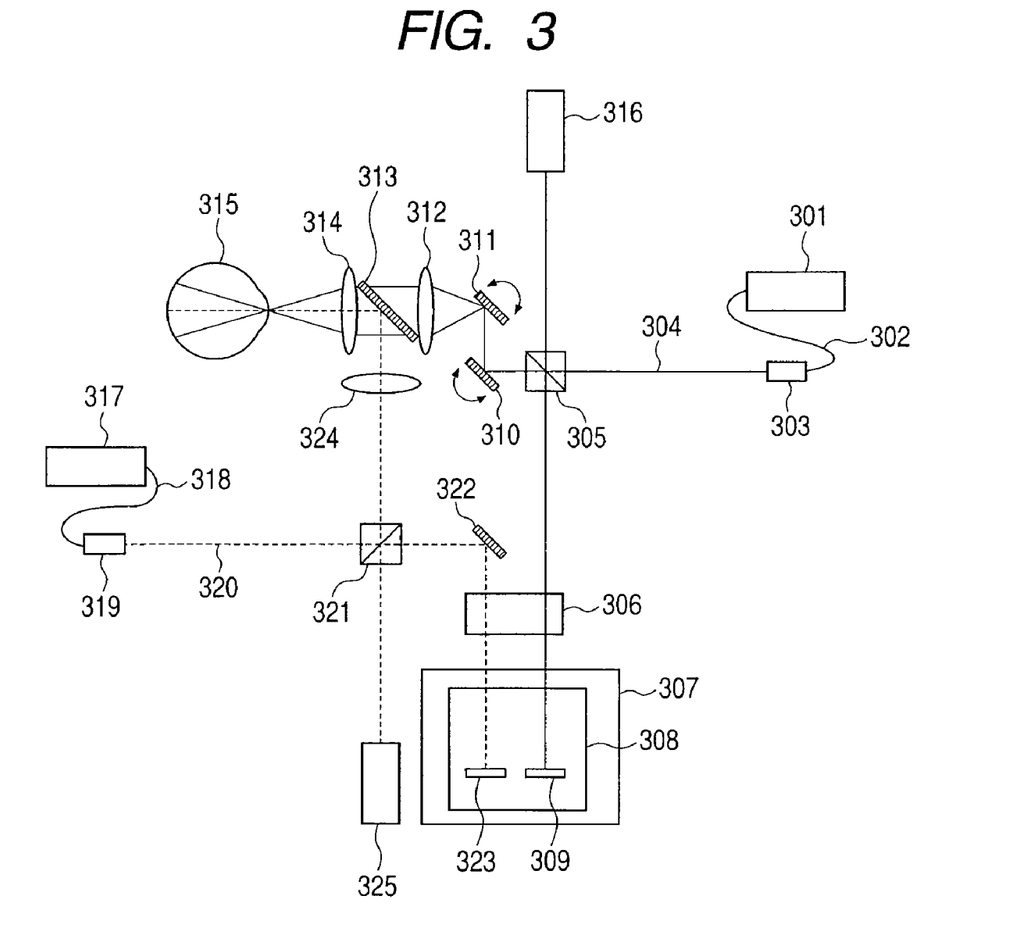
FIG. 3 is a diagram conceptually illustrating the entire configuration of an OCT device in a third embodiment according to the present invention.

An OCT device in a third embodiment will be described below. FIG. 3 is a diagram conceptually illustrating the entire configuration of an OCT device in the present embodiment. In FIG. 3, there are illustrated a low coherent light source 301 for fundus tomography, an optical fiber 302, a fiber collimator 303, a fundus photographing beam path 304, a beam splitter 305, a dispersion compensating glass 306, a reference beam path length adjusting stage 307, a tracking stage 308, a mirror 309, a galvano mirror X 310, a galvano mirror Y 311, a first lens 312, a dichroic mirror 313, a second lens 314, an eye to be inspected 315, a detector 316 for fundus tomography, a low coherent light source 317 for detecting a position of a fundus, an optical fiber 318, a fiber collimator 319, a beam path 320 for detecting a position of a fundus, a beam splitter 321, a mirror 322, a tracking mirror 323 for back and forth detecting a fundus, a third lens 324, and a fundus position detector 325. In the present embodiment, the OCT for the fundus tomography and a low coherent interferometer for detecting a back and forth motion of an eye ball use different wavelengths. The back and forth motion of a fundus is to be detected. Both of interferometers are Michelson interferometers.

Next, the configuration of an optical tomographic imaging apparatus system will be explained below. In the present embodiment, the light source 301 for tomography has a center wavelength of 840 nm, and uses an SLD light source having a half-value width of 50 nm. The beam is guided to the fiber collimator 303 by the single mode fiber 302. The beam collimated by the fiber collimator travels on the beam path 304 indicated by a solid line. The beam is split into a reference beam and a signal light by the beam splitter 305. The reference beam for the fundus tomography travels through the dispersion compensating glass 306, and then, reaches reference beam path adjusting device including the reference beam path adjusting stage 307, the tracking stage 308, and the mirrors 309 and 323.

Here, the tracking stage 308 is placed on the reference beam path adjusting stage 307. The reference beam path adjusting stage 307 is a straight stage including a stepping motor and a ball screw. The tracking stage 308 is a straight stage including a voice coil motor. The reference beam for the fundus tomography is turned over by the mirror 309, travels on the same beam path again, and returns to the beam splitter 305. Thereafter, the beam is combined with the signal light, and then, reaches the detector 316.

In contrast, the signal light obtained by splitting the beam by the beam splitter 305 reaches the eye to be inspected 315 through the lenses 312 and 314 and the dichroic mirror 313 interposed between the lenses 312 and 314 via the galvano scanners 310 and 311. The dichroic mirror transmits a beam for fundus tomography having a wavelength of about 840 nm. The functions of the scanners and the lenses are the same as those in the first and second embodiments, and therefore, its description will not be repeated below. The signal light scattered from or reflected on the fundus of the eye to be inspected travels on the same beam path, passes through the beam splitter 305, is combined with the reference beam, and reaches the detector 316. The detector detects an interference signal between the signal light and the reference beam. A flow for forming an image from the interference signal is identical to that in the first and second embodiments, and therefore, it will not be repeated here.

Next, the configuration of an anterior ocular segment position detecting optical system will be described below. The beam emitted from the light source 317 is guided to the fiber collimator 319 through the single mode optical fiber 318. The wavelength of the beam can be readily distinguished from the wavelength for the fundus tomography and the beam need not reach the fundus, and therefore, the light source has a center wavelength of 1050 nm and uses an SLD light source having a half-value width of 50 nm. A broken line 320 indicates a beam for detecting an anterior ocular segment position. The beam splitter 321 splits the beam into a reference beam and a signal light. The reference beam reaches the above-described reference beam path length adjusting device through the mirror 322 and the dispersion compensating glass 306. The reference beam turned over by the mirror 323 travels on the same beam path, and then, returns to the beam splitter 321. The beam is combined with the signal light by the beam splitter, and then, reaches to the detector 325.

In contrast, the signal light obtained by splitting the beam by the beam splitter 321 passes through the lens 324, is reflected on the dichroic mirror 313, and then, reaches the fundus of the eye to be inspected via the lens 314. The signal light reflected on or scattered from the fundus travels on the same path, and then, reaches the beam splitter 321. The beam is combined with the reference beam, and thus, reaches the detector 325. The detector 325 is a spectrometer alike in the first and second embodiments except that a line sensor is made of silicon.

Figure 6A:
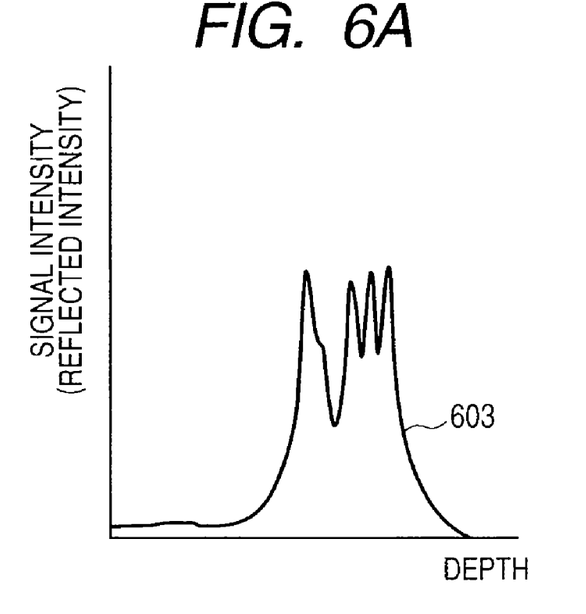
FIGS. 6A and 6B illustrate images of detection of a position of an eye ball in the third embodiment according to the present invention.
Figure 6B:
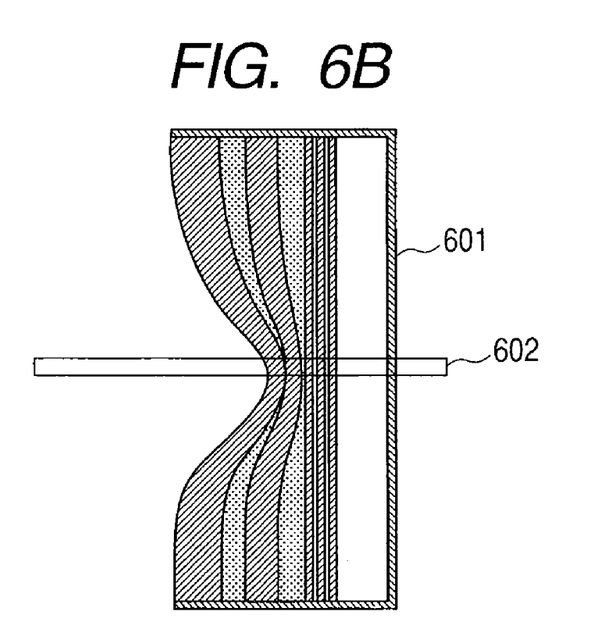

Next, a correcting method based on the anterior ocular segment position detection will be described below. FIGS. 6A and 6B illustrate an image of an output signal and a cross-sectional image of a cornea, respectively, for use in positional detection in the present embodiment. FIG. 6A illustrates a signal indicating a depth for fundus position detection. FIG. 6B illustrates a tomographic image of a fundus. There are illustrated a tomographic image 601 of a fundus, a detection beam 602, and a strength 603 of a detection signal to the depth. A signal of a reflection component at the fundus is expressed by the strength 603. The feature point of the signal 603 is obtained, and then, drive force of the stage is controlled based on the positional misplacement. A control method is the same as that in the first embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-011608, filed Jan. 22, 2009, which is hereby incorporated by reference herein in its entirety.

What is claimed is:

1. An optical tomographic imaging apparatus comprising:
    a first optical interferometer, in which a beam emitted from a first light source is split into a first measuring beam and a first reference beam, the first measuring beam being guided to an object, wherein a first tomographic image of the object is acquired by using an interference light between a return beam of the first measuring beam reflected on or scattered from the object and the first reference beam;
    a first reference beam path length changing unit configured to change a beam path length of the first reference beam;
    a second optical interferometer, in which a beam emitted from a second light source is split into a second measuring beam and a second reference beam, the second measuring beam being guided to the object, wherein a second tomographic image of the object is acquired by using an interference light between a return beam of the second measuring beam reflected on or scattered from the object and the second reference beam;
    a second reference beam path length changing unit which is provided on the beam paths of the first and second reference beams and which is configured to change beam path lengths of the first and second reference beams independently of the first beam path length changing unit;
    a detecting unit configured to detect a moving amount of the object based on the second tomographic image; and
    a controlling unit configured to control the second reference beam path length changing unit so as to change the beam path lengths of the first and second reference beams based on the moving amount.

2. The optical tomographic imaging apparatus according to claim 1, wherein the wavelength of the second light source is different from that of the first light source.

3. The optical tomographic imaging apparatus according to claim 1, wherein the object is an eye, and the detecting unit detects a back and forth position caused by a back and forth motion of a cornea of the eye.

4. The optical tomographic imaging apparatus according to claim 1, wherein the controlling unit is configured to control the second reference beam path length changing unit in a closed feedback system based on a detection result of the detecting unit, so as to reduce deformation of the first tomographic image of the object caused by a positional gap at the object.

5. The optical tomographic imaging apparatus according to claim 1,
    wherein the beam path of the second reference beam includes a part of the beam path of the first reference beam.

6. The optical tomographic imaging apparatus according to claim 5, wherein the controlling unit controls the second reference beam path length changing unit so as to reduce deformation of the first tomographic image of the object caused by a positional misplacement of the object.

7. The optical tomographic imaging apparatus according to claim 5, wherein
    the object is an eye;
    the detecting unit detects the moving amount based on a position of the eye; and
    the controlling unit controls the first reference beam path length changing unit so as to adjust the beam path length of the first reference beam with respect to the beam path length of the second reference beam based on the first tomographic image of a fundus of the eye.

8. The optical tomographic imaging apparatus according to claim 5, further comprising:
    two or more light sources for generating beams each having different wavelength bands, and
    a dichroic mirror configured to transmit one of the first and second reference beams and to reflect the other.

9. The optical tomographic imaging apparatus according to claim 5, wherein the second reference beam path length changing unit comprises:
    a mirror for reflecting the first and second reference beams; and a common stage on which the mirror is provided and which is movable along the beam paths of the first and second reference beams.

10. The optical tomographic imaging apparatus according to claim 9, wherein the detecting unit determines a presence of a feature point of the object based on the second tomographic image, and wherein the controlling unit controls the second reference beam path length changing unit so as to move the common stage, when the feature point is not present, until the feature point becomes present.

11. The optical tomographic imaging apparatus according to claim 9, wherein the common stage is a linear stage using a voice coil motor.

12. The optical tomographic imaging apparatus according to claim 5, wherein the object is an eye; and
the controlling unit controls the second reference beam path length changing unit based on an interference light of a return beam from an anterior ocular segment of the eye to which the second measuring beam is irradiated and the second reference beam, so as to reduce deformation of the first tomographic image of the object caused by a positional misplacement of the object.

13. The optical tomographic imaging apparatus according to claim 12, wherein the controlling unit is configured to control the second reference beam path length changing unit so as that an intensity of a signal from the interference light becomes substantially maximum.

14. The optical tomographic imaging apparatus according to claim 5, further comprising two or more light sources for generating beams each having different wavelength bands; and
a dichroic mirror configured to transmit one of the first and second measuring beams and to reflect the other, wherein the first and second measuring beams each have a different wavelength bands from the other.

15. The optical tomographic imaging apparatus according to claim 5, wherein a center wavelength of the first measuring beam is shorter than a center wavelength of the second measuring beam.

* * * * *